(12) United States Patent
Greeninger et al.

(10) Patent No.: US 8,014,872 B2
(45) Date of Patent: Sep. 6, 2011

(54) SYSTEM AND APPARATUS FOR CONTROLLED ACTIVATION OF ACUTE USE MEDICAL DEVICES

(75) Inventors: Daniel R. Greeninger, Coon Rapids, MN (US); David A. Dinsmoor, Saint Paul, MN (US); Vincent Larik, Kerkrade (NL); Receveur Rogier, Maastricht (NL); David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 579 days.

(21) Appl. No.: 11/343,354

(22) Filed: Jan. 31, 2006

(65) Prior Publication Data
US 2006/0190060 A1  Aug. 24, 2006

Related U.S. Application Data

(63) Continuation-in-part of application No. 10/920,818, filed on Aug. 17, 2004, now Pat. No. 7,571,008.

(60) Provisional application No. 60/495,901, filed on Aug. 18, 2003.

(51) Int. Cl.
*A61N 1/08* (2006.01)
(52) U.S. Cl. .............. 607/60; 607/34; 607/62
(58) Field of Classification Search .......... 607/16, 607/62, 34, 60
See application file for complete search history.

(56) References Cited

U.S. PATENT DOCUMENTS

| | | | | |
|---|---|---|---|---|
| 4,120,307 | A | | 10/1978 | Jirak et al. |
| 4,404,972 | A | * | 9/1983 | Gordon et al. ........ 607/16 |
| 4,408,608 | A | * | 10/1983 | Daly et al. ........ 607/57 |
| 4,590,941 | A | * | 5/1986 | Saulson et al. ........ 607/34 |
| 4,800,883 | A | * | 1/1989 | Winstrom ........ 607/7 |
| 4,917,093 | A | * | 4/1990 | Dufresne et al. ........ 607/62 |
| 5,299,569 | A | * | 4/1994 | Wernicke et al. ........ 607/45 |
| 5,304,206 | A | * | 4/1994 | Baker et al. ........ 607/2 |
| 5,476,485 | A | * | 12/1995 | Weinberg et al. ........ 607/28 |
| 5,522,865 | A | * | 6/1996 | Schulman et al. ........ 607/56 |
| 5,810,747 | A | * | 9/1998 | Brudny et al. ........ 600/595 |
| 5,916,237 | A | | 6/1999 | Schu |
| 6,215,081 | B1 | | 4/2001 | Jensen et al. |
| 6,303,885 | B1 | | 10/2001 | Hichwa et al. |
| 6,363,280 | B1 | * | 3/2002 | Mouchawar et al. ........ 607/16 |
| 6,415,181 | B1 | * | 7/2002 | Schu et al. ........ 607/16 |
| 6,700,465 | B2 | | 3/2004 | Cho |

(Continued)

FOREIGN PATENT DOCUMENTS
WO  WO2005018685 A2  3/2005

*Primary Examiner* — Scott Getzow
*Assistant Examiner* — Joseph Dietrich
(74) *Attorney, Agent, or Firm* — Carol F. Barry; Stephen W. Bauer; Evans M. Mburu

(57) ABSTRACT

An integrated activation system for an implantable medical device (IMD) sharing a power source, the activation system comprising a switching circuit having first and second inputs and having an output coupled to the acute use device, a gating element coupled to the first input and configured to gate power from the power source to the switching circuit, and a sensing element coupled to the second input of the switching circuit. The sensing element is configured to sense an activation condition, enable an operation interval of the switching circuit, and transmit a signal to the switching circuit during the activation condition. The switching circuit is configured to transmit power to the acute use device upon receipt of a pre-determined number of signals from the sensing element.

21 Claims, 4 Drawing Sheets

U.S. PATENT DOCUMENTS

| | | |
|---|---|---|
| 6,879,429 B2 | 4/2005 | Wong et al. |
| 6,917,831 B2 * | 7/2005 | Bloemer et al. ............... 607/16 |
| 7,191,012 B2 * | 3/2007 | Boveja et al. .................. 607/60 |
| 7,272,441 B1 * | 9/2007 | Chapman et al. ................ 607/5 |
| 2002/0057148 A1 | 5/2002 | Johnson et al. |
| 2003/0149459 A1 * | 8/2003 | Von Arx et al. ................ 607/60 |
| 2005/0043594 A1 | 2/2005 | Dinsmoor et al. |
| 2006/0190060 A1 | 8/2006 | Greeninger et al. |

* cited by examiner

SYSTEM AND APPARATUS FOR CONTROLLED ACTIVATION OF ACUTE USE MEDICAL DEVICES

CROSS-REFERENCE TO RELATED APPLICATIONS

This application is a continuation-in-part application of application Ser. No. 10/920,818, filed Aug. 17, 2004 now U.S. Pat. No. 7,571,008, which claims the benefit of U.S. Provisional Application No. 60/495,901, filed Aug. 18, 2003.

TECHNICAL FIELD

The present invention relates generally to medical devices, and more particularly to controlling activation of acute use medical devices.

BACKGROUND

Acute use medical devices are increasingly popular as modes for improving medical care. For example, single-use, temporary pH sensors, recoverable miniature cameras, and leadless stimulators are some acute use medical devices that are becoming pervasive tools used in medical treatment. Most of these devices are self-contained and powered by batteries to operate continuously until the battery is depleted or may intermittently operate with spaced apart "sleep" intervals so as to extend battery longevity.

In designing acute use medical devices, a trade-off is commonly encountered between competing needs for a small device size and for a battery with sufficient capacity to meet longevity goals. The battery is oftentimes the largest component in the acute use medical device and therefore significantly impacts the size of the acute use medical device.

To minimize battery size, it is generally desirable to design a device that draws a negligible amount of current until a deterministic activation occurs. Such design should also be relatively immune to inappropriate activations so as to avoid unnecessary current consumption.

Conventional reed switches have been used in the past with implantable medical devices and acute use medical devices. For example, a conventional reed switch has been used between the battery and the device circuitry of a pH sensor. As packaged, the reed switch is biased open (i.e., the device is "turned-off") by an external biasing magnet placed over the sensor during manufacture. The pH sensor is "turned-on" just prior to implantation by removing the external biasing magnet.

However, this conventional reed switch generally tends to be too large in size and thus adds significant size to the acute use medical device. Additionally, the reed switch may be susceptible to environmental effects (e.g., magnetic or mechanical) that may result in inappropriate sensor activation. MEMS reed switches are generally susceptible to the same environmental effects that may cause inappropriate activation in conventional reed switches.

Other implantable device designs have used monolithic Hall effect sensors, radio frequency (RF) signaling, and ultrasound to activate the device. Monolithic Hall effect sensors have been used in the past to change the state of a device based on a sensed magnetic event. Hall effect sensors typically require a stand-by current and are generally unsuitable as a means for turning a battery-powered device on or off. In implementations utilizing RF signaling, the implanted device "listens" continuously for a unique RF signal. RF signaling shares a similar current consumption characteristic with Hall effect sensors by generally requiring some current to be used while the device is in a stand-by mode. An ultrasound transducer has been used to turn on a switch that subsequently powers a wireless sensor containing a very small battery. In this approach, the ultrasound transducer should be in effective contact with a patient's body to appropriately activate the sensor.

Accordingly, it is desirable to provide an activation device for acute use medical devices that has relatively low or negligible current draw until a deterministic activation occurs. It is also desirable to provide an activation device for acute use medical devices that gates current to the devices while avoiding significant capacity drop to a shared power source and that does not significantly contribute to an overall size of the device. In addition, it is desirable to provide an acute use medical device having reduced susceptibility to environmental effects that may result in inappropriate activation thereof. Furthermore, other desirable features and characteristics of the present invention will become apparent from the subsequent detailed description of the invention and the appended claims, taken in conjunction with the accompanying drawings and this background of the invention.

BRIEF SUMMARY

According to various exemplary embodiments, a system and apparatus are provided that remotely activate implantable medical devices. In a first exemplary embodiment, an integrated activation system is provided for an acute use medical device sharing a power source. The activation system comprises a switching circuit having first and second inputs and having an output coupled to the acute use device, a gating element coupled to the first input and configured to gate power from the power source to the switching circuit, and a sensing element coupled to the second input of the switching circuit. The sensing element is configured to sense an activation condition, enable an operation interval of the switching circuit, and transmit a signal to the switching circuit during the activation condition. The switching circuit is configured to transmit power to the acute use device upon receipt of a pre-determined number of signals from the sensing element.

In another exemplary embodiment, an acute use medical device is provided comprising a power source, a therapy unit, a switching circuit having first and second inputs and having an output coupled to the therapy unit, a gating element having an input coupled to the power source and an output coupled to the first input of the switching circuit, and a sensing element coupled to the second input of the switching circuit. The gating element is configured to gate power to the switching circuit. The sensing element is configured to change from a first state to a second state indicating an activation condition of the acute use medical device, enable an operation interval of the switching circuit, and transmit a signal to the switching circuit during the second state. The switching circuit is further configured to transmit power to the therapy unit upon receipt of a pre-determined number of the signals from the sensing element.

In yet another exemplary embodiment, an integrated activation system for an acute use medical device sharing a power source is provided. The activation system comprises a switching circuit having a first input coupled to the power source and an output coupled to the therapy unit and having a second input, a gating element having an input coupled to the power source and an output coupled to the first input of the switching circuit, and a sensing element coupled to the second input of the switching circuit. The gating element is configured to gate power to the switching circuit during a first state. The sensing element is configured to detect a first signal indicating an activation condition, enable an operation interval of the switching circuit, and transmit a second signal to the switching circuit upon detecting the first signal. The switching circuit is configured to transmit power to the therapy unit upon receipt of a predetermined number of the second signals.

BRIEF DESCRIPTION OF THE DRAWINGS

The foregoing and other aspects and attendant advantages of the invention will become more readily appreciated as the same becomes better understood by reference to the following detailed description, when taken in conjunction with the accompanying drawings, wherein.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary, brief description of the drawings, or the following detailed description.

Figure 1:
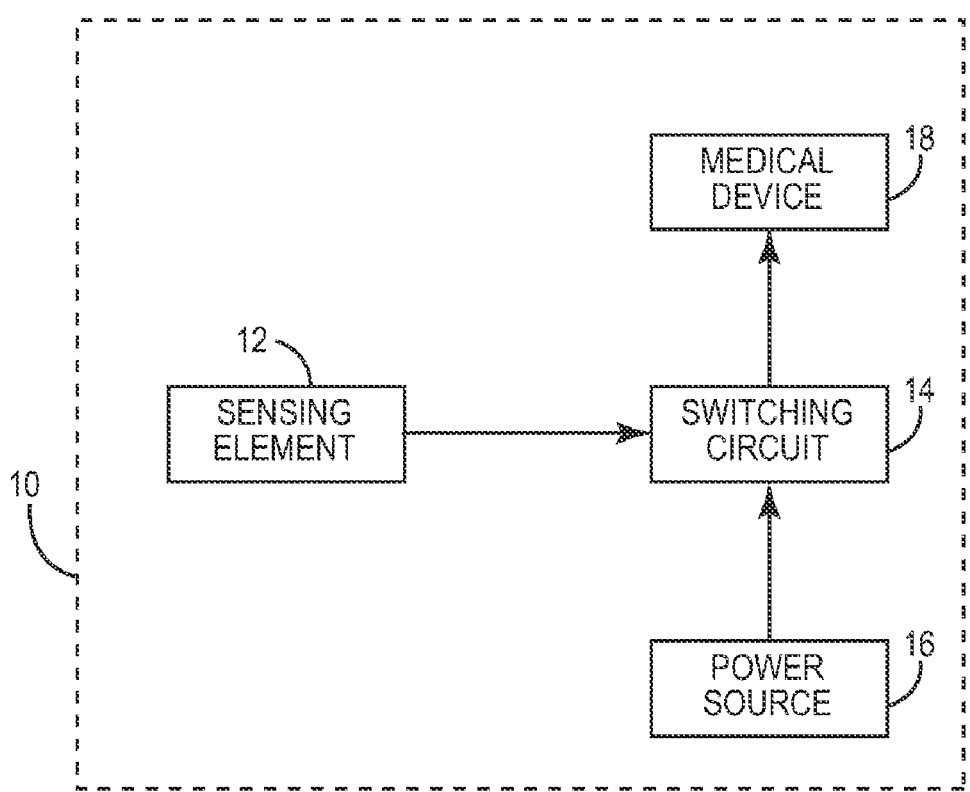
FIG. 1 is a block diagram illustrating an acute use medical device in accordance with an exemplary embodiment of the present invention.

Referring to the drawings, FIG. 1 is a block diagram illustrating an acute use medical device 10 in accordance with an exemplary embodiment of the present invention. The acute use medical device 10 comprises a sensing element 12, a switching circuit 14 coupled to the sensing element 12, and a power source 16 coupled to the switching circuit 14. A therapy Unit 18, such as a wireless pH sensor, a leadless stimulator, a miniature camera, or any number of medical devices, may be coupled to the switching circuit 14. Although not specifically detailed herein, additional components and circuitry of acute use medical devices may also be included with the acute use medical device 10. The sensing element 12 actuates the switching circuit 14 based on a desired triggering event. For example, if the selected therapy unit 18 is an implantable probe and the sensing element 12 is a MEMS reed switch, selective application of an external magnetic field by an operator to the sensing element 12 activates the MEMS reed switch 12 which in turn activates the switching circuit 14 to gate power to the implantable probe.

The sensing element 12 is configured to detect a change in the environment around the sensing element 12 and is activated upon such detection. Changes detected by the sensing element 12 include, by way of example and not limitation, a physiological change (e.g., blood chemistry pH, body temperature, etc.), a change in a magnetic field, an optical change, or other change in the environment around the acute use medical device 10. Examples of sensing elements 12 include but are not limited to Micro-Electrical Mechanical systems (MEMS) reed switches, low-voltage micro-switching devices, microrelays, thermal bimorphs, photosensors, and the like. The sensing element 12 is preferably a bi-stable MEMS switch. For example, the bi-stable MEMS switch comprises a moveable beam, a support structure (e.g., a dual spring suspension system) for the moveable beam, and an actuator for displacing (e.g., lateral displacement) the moveable beam to an "ON" position from an "OFF" position.

The sensing element 12 may be selected to have a negligible current draw on the power source 16 when inactive, i.e., when not detecting a pre-determined change in the environment around acute use medical device 10. In one exemplary embodiment, the sensing element 12 preferably has a current draw of equal to or less than about 1 nanoamp (nA) from the power source 16 when inactive, and more preferably, the sensing element 12 does not draw current from the power source 16 when inactive. Providing a sensing element that draws relatively small amounts of current or no current from a battery until a deterministic activation occurs reserves as much battery capacity for operation of the acute use medical device 10.

The power source 16 provides current to operate the sensing element 12 during activation of the same. An example of a power source includes, by way of example and not limitation, a battery. The particular current and voltage requirements of the battery 16 may vary depending on the particular therapy unit 18. Within such current and voltage requirements, the battery size is selected to minimize the size of the overall medical device 10.

In one exemplary embodiment, when the sensing element 12 is activated, the switching circuit 14 is awakened, and an operation interval, or window, is enabled in the switching circuit 14, such as by a timing circuit described in greater detail hereinbelow. The switching circuit 14 gates power to the therapy unit 18 to activate the therapy unit 18 when a pre-determined number or a pre-determined pattern of activations of the sensing element 12 occur within the operation interval.

For example, the switching circuit 14 may be configured to gate power to the therapy unit 18 after three (3) activations of the MEMS reed switch occur within the operation interval. In this example, activation of the therapy unit 18, e.g., gating power to the therapy unit 18, does not occur in the event that the three total activations of the MEMS reed switch occur beyond the operation interval. Configuration of the switching circuit 14 to gate power upon a desired number or pattern of activations of the sensing element 12 is suited to minimizing interference that may occur from the environment. The switching circuit 14 may be configured such that gating power to the therapy unit 18 occurs on any number or pattern of pre-determined number of activations within the operation interval.

Figure 2:
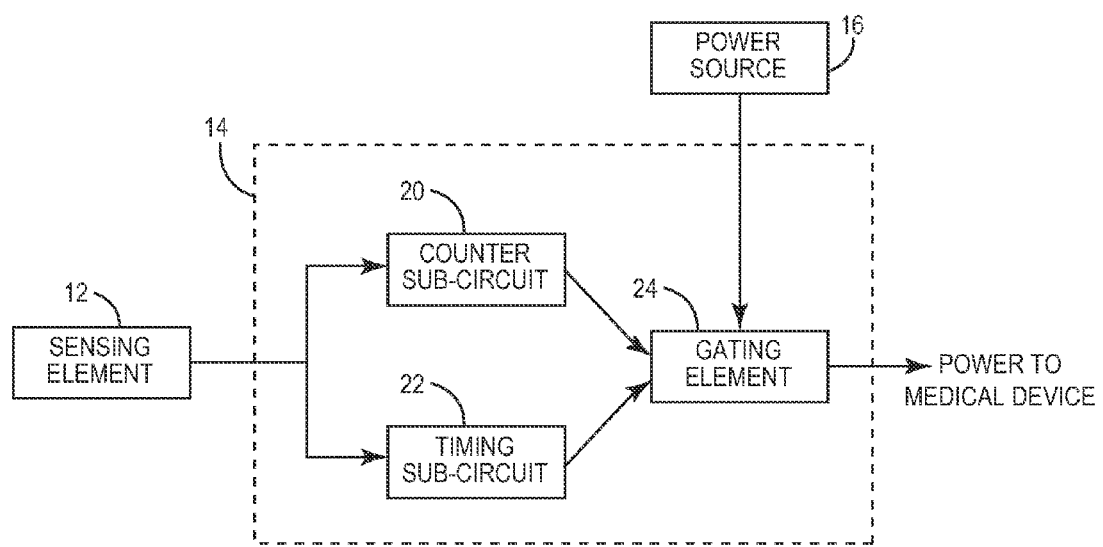
FIG. 2 is a block diagram illustrating one exemplary embodiment of the switching circuit shown in FIG. 1.

Referring to FIGS. 1 and 2, FIG. 2 is a block diagram illustrating one exemplary embodiment of the switching circuit 14 shown in FIG. 1. The switching circuit 14 and/or sensing element 12 is selected to minimize any capacity drop of the power source 16 during activation of either to reserve power for gating to the therapy unit 18. The life of the power source 16 may be extended, in comparison with conventional acute use medical devices, by minimizing the capacity drop to the power source 16 that may be result from activation of the switching circuit 14 and/or sensing element 12. In one exemplary embodiment, the switching circuit 14 includes a counter 20, a timer 22, and a gating element 24 coupled to the counter 20 and the timer 22. The switching circuit 14 may be configured as an integrated circuit (IC) such that the counter 20, timer 22, and gating element 24 are incorporated into a monolithic device. The switching circuit 14 or one or more portions thereof, such as the counter 20, timer 22, and gating element 24, may also be configured as embedded instructions or programmable instructions in a microprocessor or a microcontroller contained within or coupled to the acute use medical device 10.

The counter 20 and timer 22 are awakened by activation of the sensing element 12. This initial activation of the sensing element 12 corresponds to a new operation interval or cycle as established by the timer 22. As previously mentioned herein, the switching circuit 14 may be configured to gate power to the therapy unit 18. In this exemplary embodiment, the counter 20 may be configured to count a selected or pre-determined number of sensing element 12 activations. The counter 20 may include one or more latches, for example, to count sensing element 12 activations.

As previously mentioned, the timer 22 establishes the operation interval that serves as a basis for the switching circuit 14 to determine whether to gate power to the therapy unit 18. In one exemplary embodiment, the timer 22 includes a resistor and capacitor circuit. The values of the resistor and capacitor determine the length of the operation interval in this embodiment. Although latches are used to describe the counter 20 and a resistor and capacitor combination is used to describe the timer 22, other devices and combinations may also be used. The resulting configuration for the counter 20 and the timer is preferably selected to minimize impact on the overall size of the acute use medical device 10.

The gating element 24 controls power gated to the therapy unit 18. This gating is in response to the pre-determined number or pattern of sensing element activations, as determined by the counter 20, occurring within the operation interval established by the timer 22. In one exemplary embodiment, the gating element 24 is a transistor, such as a metal-oxide semiconductor field effect transistor (MOSFET) or a junction type field effect transistor (JFET), or a bistable MEMS switch. The transistor embodiment of the gating element 24 is suited for the monolithic device configuration of the switching circuit 14, although other types of transistors or devices may be also used, such as discrete devices, although not specifically detailed herein.

The switching circuit 14 may additionally include a feedback circuit (not shown) or other feedback mechanism that indicates to the switching circuit 14 when conditions are met for discontinuing gating of power. For example, a second sensing element may be coupled with a feedback circuit that detects for a pre-determined condition, such as a blood pH level. Upon detection of the pre-determined condition, this second sensing element is activated and triggers the feedback circuit. The feedback circuit in turn deactivates the switching circuit 14 to discontinue gating of power to the therapy unit 18.

Additionally, although gating power to the therapy unit 18 is described hereinabove with respect to activation of the sensing element 12, a more robust system for activating the acute use medical device 10 may include one or more conditions to be met prior to gating power. In one exemplary embodiment, another sensing element, e.g., a third sensing element, may be coupled to the switching circuit 14 such that the switching circuit 14 gates power to the therapy unit 18 when both the pre-determined number or pattern of sensing element activations and the third sensing element is activated within the operation interval. For example, the therapy unit 18 receives power from the power source 16 when a MEMS reed switch is activated four times and a detected temperature is about 37° C. within the operation interval.

Figure 3:
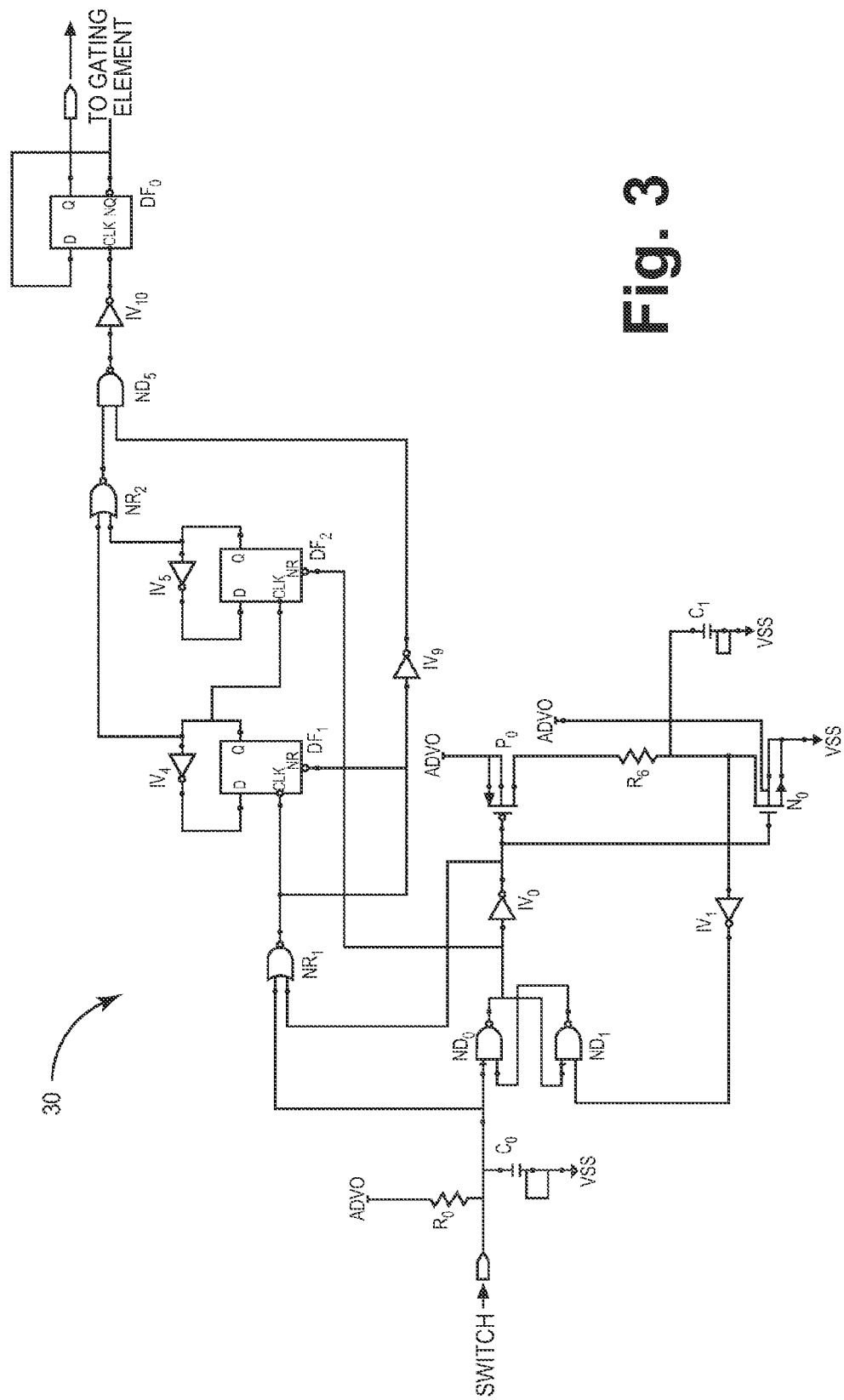
FIG. 3 is a schematic diagram of an exemplary embodiment of a switching circuit.

Referring to FIGS. 1 and 3, FIG. 3 is a schematic diagram of an exemplary embodiment of a switching circuit 30. In this exemplary embodiment, one terminal of the sensing element 12 is attached to a node SWITCH. The other terminal of the sensing element 12 may be coupled to ground. The node SWITCH is pulled high through a resistor $R_0$, and a capacitor $C_0$ provides high frequency bypass at the node SWITCH to ground. Logic NAND gates $ND_0$ and $ND_1$ form a reset-set (R-S) latch. The output of $ND_0$ is nominally low to keep a pair of series connected trigger (T) flip-flops $DF_1$ and $DF_2$ in a reset mode and a capacitor $C_1$ discharged to ground. When the output of $ND_0$ is high, such as at startup, an inverter $IV_0$ activates a Positive-channel Metal-Oxide Semiconductor (PMOS) $P_0$ and charges the capacitor $C_1$ via a resistor $R_6$. When voltage on $C_1$ reaches a switching point of an inverter $IV_1$, the R-S latch resets and the output of $ND_0$ returns to low.

A Resistor/Capacitor (RC) element formed by $R_6$ and $C_1$ is used as part of a timing mechanism to toggle the switching circuit 30 on/off. When the sensing element 12 activates, a high signal at the output of $ND_0$ sensitizes a logic NOR gate $NR_1$ to signal level changes at the node SWITCH. This sensitivity lasts for an operation interval corresponding to a time for the voltage on $C_1$ to charge to the switch point of $IV_1$. At this point, the R-S latch resets as previously discussed hereinabove. This configuration reduces a likelihood of false state changes in a flop $DF_0$.

Each activation of the sensing element 12 while $NR_1$ is sensitized (including the initial activation of the sensing element 12) activates a counter formed by $DF_1$ and $DF_2$ from 11 to 01 to 10 to 00. The switching circuit 30 continuously monitors the output state of the flip-flops $DF_1$ and $DF_2$ at a logic NAND gate $ND_5$. If the output state of the flip-flops is 00 on a rising edge of the node SWITCH, the flop $DF_0$ switches states. The output of $DF_0$ may be buffered to drive a switch that gates current to any additional circuit associated with the acute use medical device 10. Using a falling edge of the node SWITCH to change state in the counter and the rising edge to control $DF_0$ avoids races in the switching circuit 30 as the counter switches state.

In this exemplary embodiment, to gate power to the medical device 18 the switching circuit 30 must sense four activations of the sensing element 12. If these four activations are not sensed, the potential state change at the output of $DF_0$ is abandoned and the counter resets. Quiescent current consumption in this exemplary embodiment is limited to any leakage current of the devices in the switching circuit 30.

Figure 4:
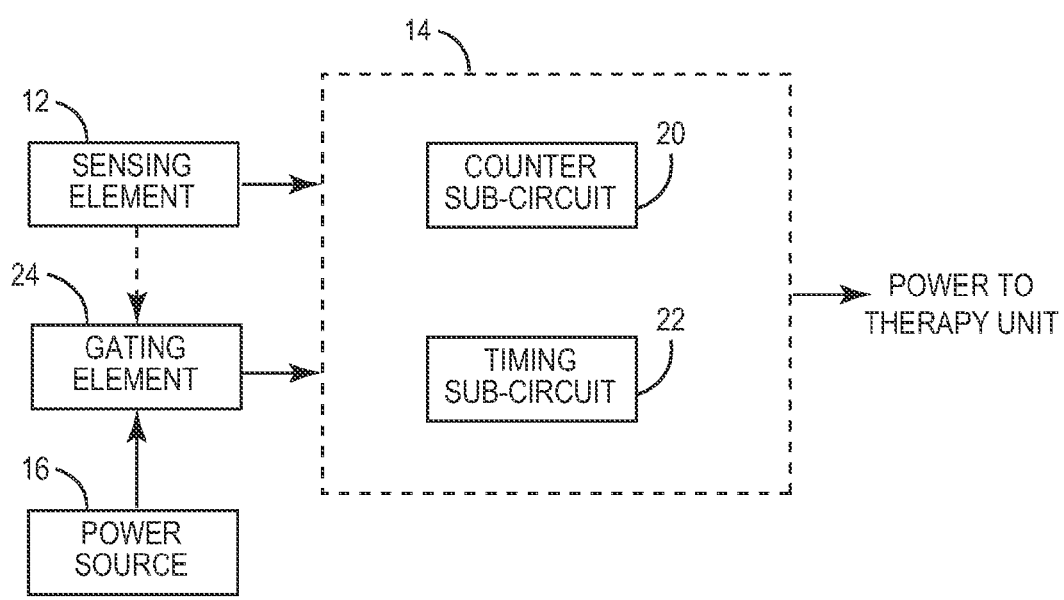
FIG. 4 is a block diagram illustrating another exemplary embodiment of the switching circuit shown in FIG. 1.

Referring to FIGS. 1 and 4, FIG. 4 is a block diagram illustrating another exemplary embodiment of the switching circuit 14 shown in FIG. 1. In this exemplary embodiment, the gating element 24 is coupled to a first input of the switching circuit 14, and the sensing element 12 is coupled to a second input of the switching circuit 14. The gating element 24 gates power from the power source 16 to the switching circuit 14. The switching circuit 14 transmits power to the therapy unit 18 upon the occurrence of any pre-determined number or pattern of activations of the sensing element 12 within the operation interval.

In an exemplary embodiment, the sensing element 12 includes a passive Radio Frequency Identification (RFID) Tag, or the like, that is activated after receiving a pre-determined Radio Frequency (RF) signal. For example, an interrogation unit having a transmitter/receiver may be used to transmit a pre-determined RF signal. The RF signal powers the sensing element 12 and the gating element 24 and switches the sensing element 12 from a non-active state to an active state. In the active state, the RF signal, or RF codes contained with the RF signal, instructs the sensing element 12 to switch the gating element 24 to an "ON" position or active state for gating power to the switching circuit 14. In an alternative embodiment, the RF signal powers the sensing element 12 and the gating element 24, and an application of a signal having a pre-determined magnetic field, or a pre-determined magnetic field flux, switches the gating element 24 to the "ON" position. In this alternative embodiment, the pre-determined magnetic field is concurrently applied during receipt of the RF signal to gate power to the switching circuit 14. The sensing element 12 and gating element 24 are thus powered independently of the acute use medical device 10.

As previously mentioned, the counter 20 and timer 22 are awakened by the activation of the sensing element 12, and the counter 20 counts a selected or pre-determined number of sensing element 12 activations (e.g., as indicated by receipt of the signal). The counter 20 may include one or more latches, for example, to count sensing element 12 activations. In another embodiment, the sensing element 12 is configured to detect a pre-determined magnetic field change and transmit the signal to the switching circuit 14 after detecting the magnetic field change.

Although power may be gated by the gating element 24 to the switching circuit 14, the switching circuit 14 remains in an "OFF" state until the pre-determined number or pattern of signals from the sensing element 12 (e.g., via an RFID signal or a magnetic field change) are detected. After the switching circuit 14 detects the predetermined number or pattern of signals from the sensing element 12, the switching circuit 14 changes to an "ON" state to transmit power from the gating element 24 to the therapy unit 18. The sensing element 12 and switching circuit 14 thus operate to prevent inadvertent activation, such as may be invoked from nearby magnetic fields, of the acute use medical device 10.

Thus, there has been provided an activation device for acute use medical devices that has relatively low or negligible current draw until a deterministic activation occurs. An activation device for acute use medical devices is also provided that gates current to the devices while avoiding significant capacity drop to a shared power source and that does not significantly contribute to an overall size of the device. Additionally, an acute use medical device is provided having reduced susceptibility to environmental effects that may result in inappropriate activation thereof.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A device activation system comprising:
a switching circuit having a first switch input adapted to receive one or more enabling signals, a second switch input adapted to receive electrical power, and an electrical power delivery output adapted to be coupled to a device to supply power to the device when a predetermined number of said one or more enabling signals are applied to said first switch input during an operation interval;
means for gating electrical power to the second switch input; and
means for sensing an environmental change external to the device activation system indicative of an activation condition of the device, generating one or more enabling signals to the switching circuit in response to the detected activation condition and enabling the operation interval of the switching circuit, and generating an activation signal to activate the electrical power gating means to provide power to the switching circuit, wherein said switching circuit is configured to remain in an "OFF" state while said gating means gates power to said switching circuit until the pre-determined number of one or more enabling signals from said sensing means are generated, and wherein said switching circuit is further configured to change to an "ON" state to apply power from said gating means to the electrical power delivery output of the switching circuit after detection of the predetermined number of one or more enabling signals within the operation interval.

2. An activation system according to claim 1, wherein said sensing means detects a pre-determined Radio Frequency (RF) signal external to the device activation system.

3. An activation system according to claim 1, wherein said sensing means detects a pre-determined magnetic field change external to the device activation system.

4. An activation system according to claim 1, wherein said sensing means comprises a sensor selected from a group consisting of a micro-electrical mechanical systems (MEMS) reed switch, a thermal bimorph, and a photosensor.

5. An activation system according to claim 1, wherein said switching circuit comprises:
a counter incremented by each enabling signal generated by the sensing means to count the number of enabling signals generated by the sensing means; and
an operation interval timer; and
wherein said switching circuit passes current from said gating means to the electrical power delivery output of the switching circuit when said counter counts a pre-determined number of said enabling signals within said operational interval.

6. An activation system according to claim 1, wherein said gating means is a transistor.

7. A medical device comprising:
a power source;
a therapy unit;
a switching circuit having first and second inputs and having an output coupled to said therapy unit;
a gate circuit having an input coupled to said power source and an output coupled to said first input of said switching circuit, said gate circuit configured to gate power to said switching circuit; and
a sensor coupled to said second input of said switching circuit, said sensor operable to:
change from a first state to a second state upon detection of a pre-determined condition external to the medical device that is indicative of an activation condition of the medical device;
enable an operation interval of said switching circuit upon detection of the pre-determined condition;
transmit an activation signal to the gate circuit to gate power to the switching circuit; and
transmit a signal to said switching circuit during said second state, said switching circuit applying power to said therapy unit upon receipt of one or more pre-determined transmitted signals from said sensor within the operation interval, wherein said switching circuit is configured to remain in an "OFF" state while said gate circuit gates power to said switching circuit until the one or more pre-determined signals from said sensor are generated, and wherein said switching circuit is further configured to change to an "ON" state to apply power from said gate circuit to the output of the switching circuit coupled to the therapy unit after detection of the one or more pre-determined signals within the operation interval.

8. A medical device according to claim 7, wherein said sensor changes from said first state to said second state upon detecting a magnetic field change external to the medical device.

9. A medical device according to claim 7, wherein said sensor changes from said first state to said second state upon receipt of a Radio Frequency (RF) signal external to the medical device.

10. A medical device according to claim 7, wherein said therapy unit comprises a miniature camera.

11. A medical device according to claim 7, wherein said therapy unit is a stimulator.

12. A medical device according to claim 11, wherein said therapy unit comprises a second sensor.

13. A medical device according to claim 7, wherein said sensor is selected from a group consisting of a micro-electrical mechanical systems (MEMS) reed switch, a thermal bimorph, and a photosensor.

14. A medical device according to claim 7, wherein said switching circuit comprises:
    a counter operable to count sensor changes of state; and
    a timer operable to establish said operation interval.

15. A medical device according to claim 14, wherein said counter comprises at least one latch device and at least one T flip-flop device.

16. A medical device according to claim 7, wherein said sensor is operable to draw zero current from said power source during said first state.

17. A medical device according to claim 7, wherein said pre-determined condition is a pH value.

18. A medical device according to claim 7, wherein said therapy unit comprises a pH sensor.

19. An integrated activation system for an acute use device, the activation system comprising:
    a power source;
    a switching circuit having a first input coupled to the power source, a second input, and an output adapted to be coupled to an acute use device;
    a gating circuit having first and second inputs and an output, said first input of said gating circuit coupled to said power source, said output of said gating circuit coupled to said first input of said switching circuit, said gating circuit configured to gate power to said switching circuit during a first gating state; and
    a sensor coupled to said second input of said switching circuit and said second input of said gating circuit and configured to:
        detect a first signal corresponding to an environmental change external to the integrated activation system that is indicative of an activation condition associated with the acute use device;
        enable an operation interval of said switching circuit upon detection of the activation condition;
        enable the gating circuit to gate power to the switching circuit upon detection of the first signal; and
        transmit a second signal to said switching circuit upon detecting said first signal, said switching circuit configured to transmit power received from said gating circuit to said switching circuit output upon receipt of a predetermined number of said second signals within the operation interval,
    wherein said switching circuit is configured to remain in an "OFF" state while said gating circuit gates power to said switching circuit until the pre-determined number of second signals from said sensor are generated, and further wherein the switching circuit is configured to change to an "ON" state to apply power from said gating circuit to the output adapted to be coupled to the acute use device after detection of the predetermined number of second signals by the switching circuit within the operation interval.

20. An integrated activation system according to claim 19, wherein said first signal is a pre-determined RF signal having an RF code, and wherein said sensor is further configured to switch said gating circuit to said first gating state upon detecting said RF code, said pre-determined RF signal powering said sensor and said gating circuit.

21. An integrated activation system according to claim 19, wherein said first signal is a pre-determined magnetic field.

* * * * *

UNITED STATES PATENT AND TRADEMARK OFFICE
CERTIFICATE OF CORRECTION

| | | |
|---|---|---|
| PATENT NO. | : 8,014,872 B2 | Page 1 of 1 |
| APPLICATION NO. | : 11/343354 | |
| DATED | : September 6, 2011 | |
| INVENTOR(S) | : Daniel R. Greeninger et al. | |

It is certified that error appears in the above-identified patent and that said Letters Patent is hereby corrected as shown below:

Column 8, Line 32-33, "...said operational interval.", should read --said operation interval.--

Signed and Sealed this
Sixth Day of December, 2011

David J. Kappos
*Director of the United States Patent and Trademark Office*